United States Patent [19]

Fukui et al.

[11] 4,082,458

[45] Apr. 4, 1978

[54] DENSITOMETER

[75] Inventors: Takashi Fukui; Hirobumi Enomoto, both of Minami-ashigara, Japan

[73] Assignee: Fuji Photo Film Co., Ltd., Minami-ashigara, Japan

[21] Appl. No.: 721,219

[22] Filed: Sep. 8, 1976

[30] Foreign Application Priority Data

Sep. 8, 1975 Japan .................................. 50-108642

[51] Int. Cl.$^2$ ..................... G01N 21/22; G01N 21/48; G02B 7/00
[52] U.S. Cl. ....................................... 356/73; 350/78; 356/201; 356/209
[58] Field of Search ........................ 356/73, 201–203, 356/209–212, 186, 173; 350/91, 236, 78, 79; 250/574

[56] References Cited

U.S. PATENT DOCUMENTS

| | | | |
|---|---|---|---|
| 2,059,781 | 11/1936 | Ellestad | 350/91 |
| 3,244,062 | 4/1966 | Sweet | 356/203 |
| 3,762,817 | 10/1973 | Harklau | 356/73 |
| 3,814,523 | 6/1974 | Abe | 356/209 |
| 3,999,860 | 12/1976 | Demsky et al. | 356/173 |

FOREIGN PATENT DOCUMENTS

| | | | |
|---|---|---|---|
| 217,168 | 12/1909 | Germany | 350/91 |
| 476,803 | 12/1937 | United Kingdom | 350/91 |

OTHER PUBLICATIONS

Altman et al. "A Microdensitometer for Reflecting Samples" Photographic Science & Technique, 2-1957, pp. 10–12.

*Primary Examiner*—John K. Corbin
*Assistant Examiner*—Wm. H. Punter
*Attorney, Agent, or Firm*—Fleit & Jacobson

[57] ABSTRACT

A densitometer which measures reflection optical density and transmission optical density has a lens barrel comprised of a fixed portion and a movable portion. The movable portion is slidably engaged with the fixed portion and movable up and down. When the density is measured, the lower end of the movable portion is put into contact with the surface of a sample to be measured. The fixed portion and the movable portion of the lens barrel is comprised of an inner cylinder and an outer cylinder extending coaxially with each other. A flux of light for illuminating the surface of the sample is guided between the inner and outer cylinders and condensed on the surface of the sample. The light reflected by the sample is guided through the inner cylinder. The inner cylinder has a collimator lens for collimating the light from the sample in the movable portion thereof and a focusing lens for focusing the collimated light on a photodetector in the fixed portion thereof, so that the light from the sample is always focused on the photodetector regardless of the position of the movable portion.

10 Claims, 3 Drawing Figures

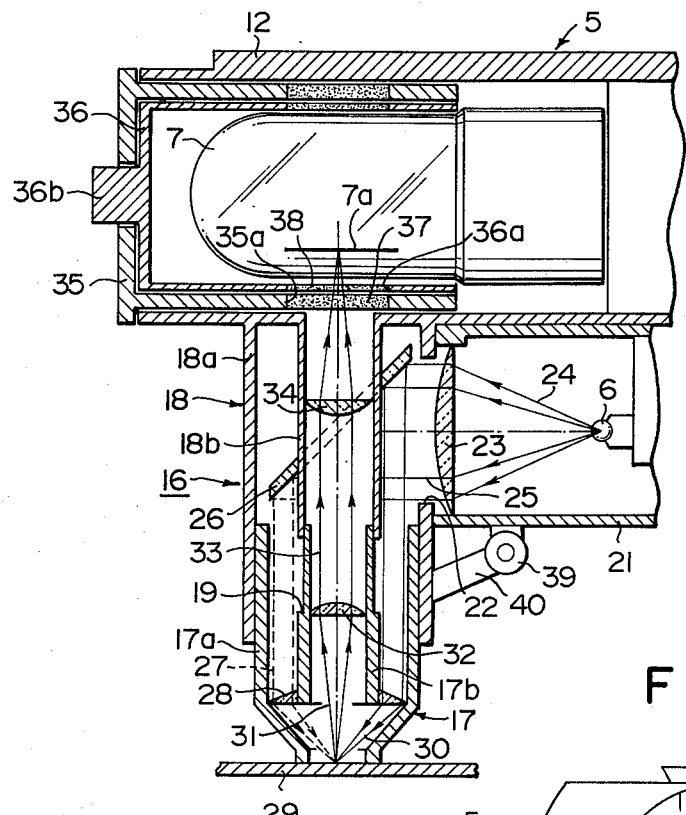
FIG.2
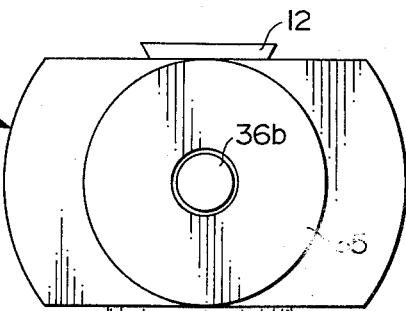
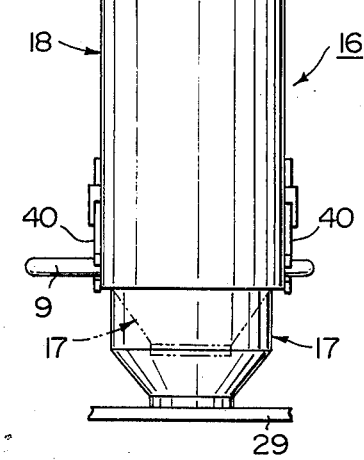
FIG.3

DENSITOMETER

BACKGROUND OF THE INVENTION

1. Field of the Invention

This invention relates to a densitometer, and more particularly to a densitometer to be used for measuring the transmission optical density and the reflection optical density of various kinds of sheet material such as photographic film, photographic paper, printed paper or the like.

2. Description of the Prior Art

The Macbeth model densitometer (made by Kollmorgen Corp.) is one of this type of densitometer adapted to measure the optical density of a photographic material. The Macbeth densitometer includes a transmission densitometer and a reflection densitometer which are separately used. The reflection densitometer employs a double cylinder structure in which a light source is provided within the inner cylinder to illuminate a sample at a right angle with respect to the surface thereof and the light reflected by the sample in the direction inclined at 45° with respect to the surface thereof is collected by a mirror attached to the inner surface of the outer cylinder and directed to a photodetector. When measuring the optical transmission density, a measuring head is moved as a whole in the direction of the optical axis and put into contact with the surface of the sample. The transmission densitometer of this type has a condenser lens at the top of a lens barrel thereof, which is movable in the direction of the optical axis. When measuring, the top of the lens barrel is put into contact with the surface of a sample and a parallel flux of light of illumination is irradiated on and through the sample from the back thereof.

The above described Macbeth densitometer is disadvantageous in that the transmission optical density and the reflection optical density must be measured with separate densitometers. In view of this defect, a Quantascan densitometer (made by Quantametric Devices Inc.) has been developed which is able to measure both the transmission and reflection optical density with a single densitometer. The Quantascan densitometer employs a double cylinder structure in which a conical mirror provided on the inner surface of the outer cylinder reflects the illumination light from a light source toward the surface of a sample and the light reflected by the surface of the sample is guided through the inner cylinder to a photodetector, and the sample is illuminated from the back thereof with a condensed flux of light and the light transmitted through the sample is guided through the inner cylinder to a photodetector. The Quantascan densitometer has a defect in that the measuring head including the double structure cylinder is not movable, and accordingly, the density is not accurately measured when the surface of the sample is light diffusive or when the thickness thereof changes. When the reflection density is measured, the area of the sample illuminated and measured varies as the thickness of the sample varies. When the transmission density is measured, the distance between the surface of the sample and the lens which receives light passing through the sample varies as the thickness of the sample changes. In other words, as the thickness of the sample increases, the angle of light incident to the light receiving lens increases and accordingly the amount of light received is increased, thus the density measured is lowered. Further, since the lower end of the lens barrel is separated from the surface of the sample, the measurement will be inaccurate if the surface of the sample is curled or waved.

SUMMARY OF THE INVENTION

In view of the defects inherent in the conventional densitometers, the primary object of the present invention is to provide a densitometer which is capable of measuring both transmission and reflection optical density with high accuracy.

Another specific object of the present invention is to provide a densitometer which performs highly accurate measurement regardless of the thickness or the state of surface of samples.

Still another object of the present invention is to provide a densitometer which is easily movable to position the optical arrangement thereof at an appropriate position relative to the surface of the sample.

The above objects of the invention are accomplished by dividing a lens barrel into a fixed portion and a movable portion guided therealong. The movable portion has a double cylinder structure comprised of an inner cylinder and an outer cylinder between which is provided a condenser optical system having a condensing point at the center of the aperture at the top of the movable portion. The outer cylinder is extended downward to form an aperture at the lower end thereof which is to be put into contact with the surface of a sample. The inner cylinder is provided with a collimator lens which has its focusing point at said center of the aperture. When measuring the density, the lower end of the outer cylinder of the movable portion is put into contact with the surface of the sample so as to position the collimator lens within the inner cylinder at a fixed position with respect to the surface of the sample, whereby the optical density of the sample can be measured with high accuracy regardless of the thickness thereof. Further, when the surface of the sample is curled or waved, the surface is flattened by the end of the cylinder to ensure accurate measurement of the optical density thereof.

BRIEF DESCRIPTION OF THE DRAWING

FIG. 2 is a longitudinal sectional view showing the internal structure of the measuring head of the densitometer as shown in FIG. 1, and FIG. 3 is a front view of the measuring head thereof.

DESCRIPTION OF THE PREFERRED EMBODIMENT

Figure 1:
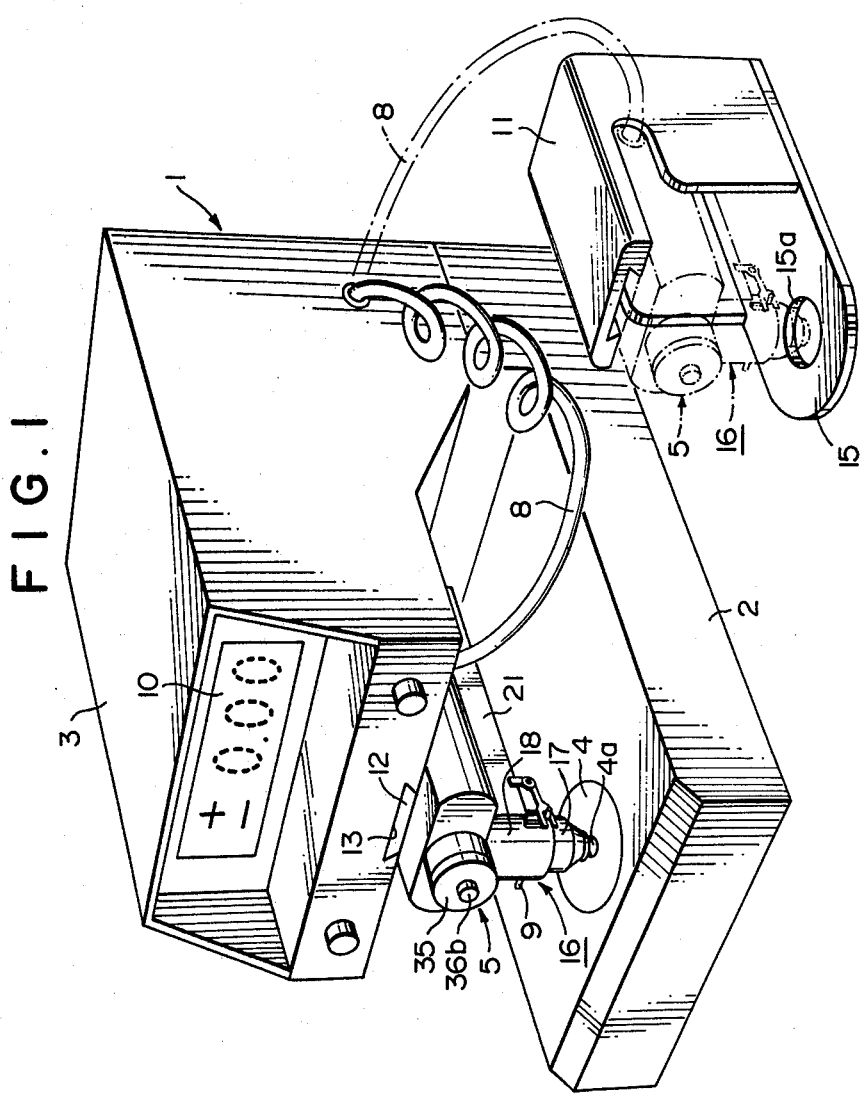
FIG. 1 is a perspective view of an embodiment of the densitometer in accordance with the present invention.

Referring to FIG. 1 which shows the external appearance of a preferred embodiment of the present invention, a densitometer body 1 is comprised of a sample table portion 2 on which samples are placed for measurement and a measuring portion 3 which includes various density measuring means. The measuring portion 3 extends above and substantially in parallel to the sample table portion 2. Within the sample table 2 are provided an illumination light source for transmission density measurement and an illumination optical system including a condenser lens. A circular sample table 4 is provided on the upper face of the sample table portion 2. The sample table 4 has a circular aperture 4a at the center thereof through which the illumination light from the light source in the sample table portion 2 passes when the transmission optical density of the sample placed on the sample table 4 is measured. Above the sample table 4 is located a measuring head 5 which receives light transmitted through or reflected from the sample placed on the sample table 4. The measuring head 5 includes a light source 6 for reflection density measurement and a photodetector 7 as will be described in detail hereinafter with reference to FIG. 2. The measuring head 5 is removable from said measuring portion 3 of the densitometer body 1 and is connected therewith by means of a cable 8. The measuring head 5 has a movable portion 17 which is moved up and down by operating a lever 9 provided on the head 5. The lever 9 is pressed downward to move the movable portion 17 of the measuring head 5 into contact with the surface of the sample placed on the sample table 4. By further pressing the lever 9 downward, a lead switch is closed and an electric circuit within the measuring portion 3 is activated to measure the density and indicate the measured density on a digital indicator 10 provided on the front face of the measuring portion 3.

The measuring head 5 of the densitometer in accordance with the present invention is movable upward to a position of about 10cm above the sample table 4. When the densitometer is used to measure the density of a sample which has a thickness larger than 10cm, the measuring head 5 is removed from the measuring portion 3 and is mounted on a support device 11 which has a base plate 15 with an aperture 15a. The base plate 15 is placed on the surface of the material to be measured. To state in more detail, the measuring head 5 has a protrusion 12 with a dove-tail shaped cross-section on the top face thereof which is in slidable engagement with a groove 13 formed on the lower face of the measuring portion 3. The support 11 also has a groove with which the protrusion 12 of the measuring head 5 is engageable.

Now the preferred embodiment of the present invention will be described in detail with reference to FIGS. 2 and 3. A lens barrel 16 is comprised of a movable portion 17 which is axially movable up and down, and a fixed portion 18 which guides the axial movement of the movable portion 17. The movable portion 17 is comprised of an outer movable cylinder 17a and an inner movable cylinder 17b, and the fixed portion 18 is comprised of an outer fixed cylinder 18a and an inner fixed cylinder 18b. The movable cylinders 17a and 17b are slidable along the fixed cylinders 18a and 18b, respectively. The inner movable cylinder 17b has a stepped portion 19 which abuts on the lower end of the inner fixed cylinder 18b to limit the range of up and down movement of the movable portion 17.

A light source chamber 21 which retains therein a light source 6 for reflection density measurement and a collimator lens 23 having a focal point at said light source 6 is connected with the outer fixed cylinder 18a of the fixed portion 18. The light source chamber 21 extends radially from an opening 22 of the outer fixed cylinder 18a. A flux of light 24 emitted from the light source 6 is collimated through the collimator lens 23, and the collimated light 25 passes through the opening 22 and is reflected toward the lower portion of the measuring head 5 by an annular mirror 26 provided in the outer fixed cylinder 18a of the lens barrel 16 and inclined at 45° with respect to the fixed cylinders 18a and 18b. The flux of light 27 reflected by the mirror 26 has a C-shaped cross-section since a part of the flux of light 25 from the lens 23 is intercepted by the inner fixed cylinder 18b. The mirror 26 could also be C-shaped.

The outer movable cylinder 17a is extended downward beyond the inner movable cylinder 17b and is tapered. Between the outer and inner movable cylinders 17a and 17b is provided an annular condenser 28 to direct the flux of light 27 from the mirror 26 toward the surface of a sample 29 at an angle 45° with respect thereto as shown at 30. The annular condenser 28 may not be a lens, but a prism or conical mirror so long as it directs the flux of light 27 from the mirror 26 to the surface of the sample 29 at the angle 45° and uniformly distributes the light on the surface of the sample 29. A Fresnel lens may be used as the annular condenser 28.

Within the inner movable cylinder 17b is provided a collimator lens 32 which collimates light 31 reflected by the surface of the sample 29. The light from the annular condenser 28 is reflected by the surface of the sample 29, and the light reflected by the sample in the direction substantially parallel to the optical axis of the collimator lens 32 is collimated through the collimator lens 32 and then the collimated flux of light 33 is focused on a light receiving plane 7a of a photodetector 7 such as a photomultiplier tube through a focusing lens 34 which is provided in the inner fixed cylinder 18b.

The photodetector 7 is installed in a filter housing 35 in which a filter casing 36 is rotatably provided. The filter housing 35 has a plurality of, e.g. seven, apertures 35a in which color separating spectroscopic filters 37 are inserted to measure the spectroscopic optical density. For instance, red, green, blue, cyan, yellow, magenta and sight sensitivity measuring color filters are employed. By rotating the filter housing 35, an appropriate filter 37 is brought into alignment with the optical axis of the focusing lens 34 in the inner fixed cylinder 18b. The filter casing 36 has a rectangular or elongated aperture 36a in which an attenuator 38 such as a neutral density (ND) filter or a mesh filter is mounted. The attenuator 38 has a continuously varying transmission density from one end to the other so that the quantity of light passing therethrough can be varied by rotating the filter casing 36. For instance, the attenuator 38 may be an optical wedge.

With reference to FIGS. 2 and 3, a bearing 39 on which a pair of arms 40 are pivotally mounted is provided beneath the light source chamber 21. Said lever 9 is mounted on the arms 40 and is made movable up and down to move the movable portion 17. The movable portion 17 is normally held in its upper position as shown with chain lines in FIG. 3 and is moved downward up to a position where the lower end of the outer movable cylinder 17a is put into contact with the surface of the sample 29 by pressing the lever 9 downward when the density is measured.

Now the operation of the above described embodiment will be described in detail. When the sample 29 to be measured has a thickness not larger than 10cm, the measurement is conducted with the measuring head 5 mounted on the densitometer body 1. The sample 29 is placed on the aperture 4a of the sample table 4, and the filter housing 35 and the filter casing 36 are operated to select a proper filter of density and color.

When the reflection optical density is to be measured, the light source 6 for reflection density measurement is turned on and the movable portion 17 of the lens barrel 16 is moved down to the position indicated with solid lines from the position indicated with chain lines in FIG. 3 by means of the lever 9. Thus, the lower end of the outer cylinder 17a of the movable portion 17 is put into contact with the surface of the sample 29 placed on the sample table 4 to correct the curl or wave of the sample 29. The flux of slight 24 from the light source 6 is collimated through the collimator lens 23 and the collimated flux of light 25 is reflected downward by the mirror 26. The flux of light 27 reflected by the mirror which is collimated passes through the annular space between the outer and inner fixed cylinders 18a and 18b and between the outer and inner movable cylinders 17a and 17b. The flux of light 27 is then refracted by the annular condenser 28 and condensed on the surface of the sample 29. The incident angle of the flux of light 30 condensed through the annular condenser 28 is substantially 45°. A part of the light reflected by the surface of the sample 29 is reflected in the direction substantially normal to the surface of the sample 29. The light reflected in the normal direction 31 is collimated through the collimator lens 32 in the inner movable cylinder 17b. The collimated flux of light 33 is condensed through the focusing lens 34 and focused on the light receiving plane 7a of the photodetector 7 by way of a color separating spectroscopic filter 37 in the color density measuring filter housing 35 and an attenuator 38 in the filter casing 36.

By depressing the lever 9 further downward after the lower end of the outer movable cylinder 17a is put into contact with the surface of the sample 29, a lead switch is turned on to actuate the electric circuit and indicate the density measured through the photodetector 7 and the electric circuit connected therewith on the digital indicator 10. Thus, the reflection optical density of the sample 29 is indicated in digital form on the indicator 10.

When the transmission optical density is to be measured, a light source (not shown) provided under the sample table 4 is turned on and the lever 9 is moved down to put the lower end of the outer movable cylinder 17a into contact with the surface of the sample 29 placed on the sample table 4. The flux of light from the light source under the sample table 4 is condensed by use of a condenser (not shown) and irradiated on the back of the sample 29 through the aperture 4a of the sample table 4, and is transmitted through the sample 29. A part of the light transmitted through the sample 29 is incident to the collimator lens 32 and finally received by the photodetector 7. Thus, the transmission optical density is indicated on the digital indicator 10 in the manner similar to the manner employed in the above described operation to indicate the reflection optical density.

When the thickness of the sample is 10cm, the measuring head 5 is separated from the densitometer body 1 and mounted on the support device 11 as shown with chain lines in FIG. 1. The base plate 15 of the support device 11 is put on the sample and the lever 9 is moved down similarly to the above described operation.

The results of the performance of the densitometer in accordance with the present invention are indicated in the following table in comparison with the results obtained by a conventional densitometer which has a non-movable measuring head. The following table shows that the measurement is not influenced by the thickness in case of the densitometer of this invention, whereas it is influenced by the thickness of the sample in the conventional densitometer.

| Standard Density (Sample) | This Invention Thickness (mm) | | | Densitometer with Non-movable Head Thickness (mm) | | |
| --- | --- | --- | --- | --- | --- | --- |
| | 0.5 | 1 | 2 | 0.5 | 1 | 2 |
| 0.1 | 0.1 | 0.1 | 0.1 | 0.16 | 0.28 | 0.38 |
| 0.35 | 0.35 | 0.35 | 0.35 | 0.42 | 0.50 | 0.65 |
| 0.72 | 0.73 | 0.72 | 0.72 | 0.72 | 0.84 | 0.97 |
| 1.10 | 1.10 | 1.10 | 1.10 | 1.12 | 1.20 | 1.34 |
| 1.40 | 1.39 | 1.40 | 1.41 | 1.44 | 1.50 | 1.66 |

We claim:

1. A densitometer which has a double structured lens barrel comprised of an inner cylinder and an outer cylinder extending coaxially therewith in which an annular light passage is formed between the inner and outer cylinders, a flux of light between the cylinders is condensed on the front face of a sample through a condenser optical system provided between said cylinders when reflection optical density of the sample is measured, the back face of the sample is illuminated with a flux of light from a light source located under the sample when transmission optical density of the sample is measured, and the light reflected by or transmitted through the sample is guided to a photodetector through said inner cylinder, the improvement comprising a fixed portion and a movable portion which constitute said double structured lens barrel, said movable portion being slidably engaged with the fixed portion and movable in the direction of the optical axis of lenses installed therein, said movable portion including an inner movable cylinder, an outer movable cylinder coaxially extending therewith and extending downward therebeyond and having an open lower end, said fixed portion including an inner fixed cylinder and an outer fixed cylinder extending coaxially therewith, said inner and outer movable cylinders of said movable portion being slidably engaged with said inner and outer fixed cylinders of the fixed portion, a condenser optical system provided between said inner and outer movable cylinders for normally condensing a flux of parallel light therebetween to a point at the center of said open lower end of the outer movable cylinder regardless of the position of the movable portion, a collimator lens provided in said inner movable cylinder which has a focusing point at said point at the center of the open lower end of the outer movable cylinder, and a light source chamber which includes a light source for reflection density measurement connected with the fixed portion, said light source chamber including a light source and a collimator lens having an optical axis being perpendicular to the optical axis of said collimator lens in said inner movable cylinder and means for moving said open lower end of the outer movable cylinder into contact with the surface of a sample during the measurement of the optical density of the sample.

2. A densitometer as claimed in claim 1 wherein a substantially annular mirror is provided between said inner and outer fixed cylinders of the fixed portion for reflect light from said light source chamber downward along the cylinders.

3. A densitometer as claimed in claim 2 wherein said mirror is C-shaped and inclined at 45° with respect to the optical axis of the collimator lens of the light source chamber.

4. A densitometer as claimed in claim 1 wherein the densitometer comprises a densitometer body and a removable measuring head which includes said lens barrel, whereby the removable measuring head is removed from said densitometer body when desired.

5. A densitometer as claimed in claim 4 wherein the densitometer further comprises a support device provided separately from the densitometer body for supporting said removable measuring head when the measuring head is removed from the densitometer body.

6. A densitometer as claimed in claim 1 wherein said densitometer has a photodetector, and said inner fixed cylinder is provided with a focusing lens which focuses a flux of collimated light from said collimator lens in said inner movable cylinder on said photodetector.

7. A densitometer as claimed in claim 6 wherein a filter means is provided between said focusing lens and said photodetector.

8. A densitometer as claimed in claim 7 wherein the density of said filter is changeable.

9. A densitometer as claimed in claim 7 wherein the color of said filter is changeable.

10. A densitometer as claimed in claim 9 wherein said filter comprises a selectable plurality of filters of different color.

* * * * *